(12) United States Patent
Bazylenko

(10) Patent No.: US 7,768,650 B2
(45) Date of Patent: Aug. 3, 2010

(54) OPTOELECTRONIC BIOCHIP

(76) Inventor: Michael Bazylenko, 68 Headland Rd, North Curl Curl, NSW (AU) 2099

( * ) Notice: Subject to any disclaimer, the term of this patent is extended or adjusted under 35 U.S.C. 154(b) by 340 days.

(21) Appl. No.: 10/566,482

(22) PCT Filed: Apr. 20, 2005

(86) PCT No.: PCT/AU2005/000552

§ 371 (c)(1), (2), (4) Date: Jan. 31, 2006

(87) PCT Pub. No.: WO2005/103652

PCT Pub. Date: Nov. 3, 2005

(65) Prior Publication Data

US 2006/0197960 A1 Sep. 7, 2006

(30) Foreign Application Priority Data

Apr. 21, 2004 (AU) ............................... 2004902122

(51) Int. Cl.
*G01B 9/02* (2006.01)
*C12M 1/00* (2006.01)
*C12M 1/34* (2006.01)
*C12M 3/00* (2006.01)

(52) U.S. Cl. ................. 356/491; 435/283.1; 435/287.2; 435/288.7; 422/82.5; 977/701; 977/702; 977/707; 977/712

(58) Field of Classification Search ...................... 257/7; 356/491; 385/12; 435/283.1, 287.2; 436/172, 436/527, 532; 438/691
See application file for complete search history.

(56) References Cited

U.S. PATENT DOCUMENTS

| | | | | |
|---|---|---|---|---|
| 6,110,749 A * | 8/2000 | Obremski et al. ............ 436/527 |
| 6,203,985 B1 * | 3/2001 | Jiang et al. ..................... 435/6 |
| 6,214,733 B1 * | 4/2001 | Sickmiller .................. 438/691 |
| 6,395,558 B1 * | 5/2002 | Duveneck et al. ........... 436/172 |
| 7,186,567 B1 * | 3/2007 | Sutherland et al. .......... 436/532 |
| 7,430,039 B2 * | 9/2008 | Sugita .......................... 356/39 |
| 2003/0104481 A1 * | 6/2003 | McFarland et al. ........... 435/7.1 |
| 2004/0101861 A1 * | 5/2004 | Little et al. ..................... 435/6 |

OTHER PUBLICATIONS

Kunz et al, Sensing pads for hybrid and monolithic integrated optical immunosensors, 1994, SPIE, 2331, pp. 2-17.*

* cited by examiner

*Primary Examiner*—Robert T Crow
*Assistant Examiner*—Narayan K Bhat

(57) ABSTRACT

The present invention provides a biochip for testing biological substances comprising a plurality of binding sites, optical means for determining a specific binding event at each binding site, wherein the plurality of binding sites and the means for determining a specific binding event at each binding site are monolithically integrated into a single chip which is electrically powered and produces electrical signals in response to binding events at each binding site. The means for determining a specific binding event can include a micro-cavity light source formed in a semiconductor layer and a photodetector formed in the same semiconductor layer and further include a grating assisted vertical planar waveguide coupler for in-situ monitoring hybridization dynamics at each binding site via associated changes in refractive index. The invention further provides a method of manufacturing a biochip containing light sources, photodetectors, binding sites and optical means for determining a specific binding event at each binding site wherein said light sources, photodetectors, binding sites and optical means for determining a specific binding event at each binding site are produced by processing a single planar substrate in a sequence of deposition, photolithography and etching steps.

12 Claims, 10 Drawing Sheets

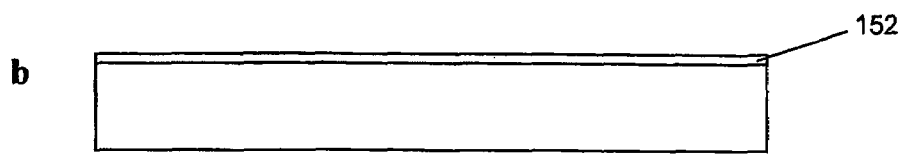
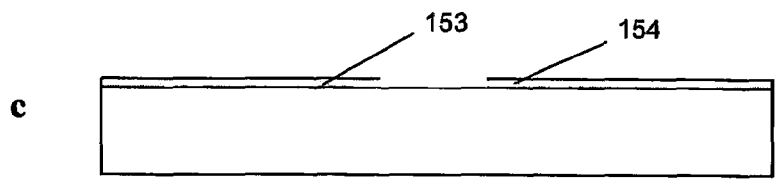
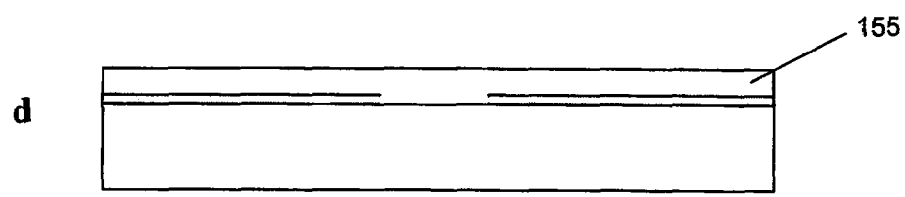
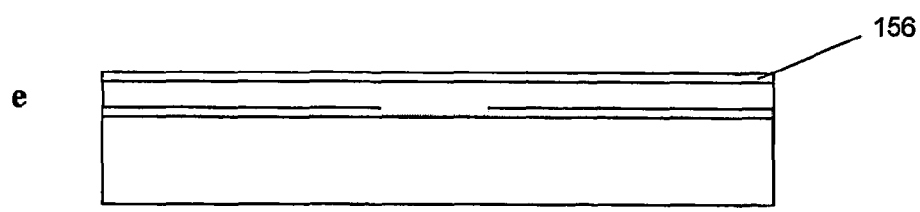
Figure 15 a-e

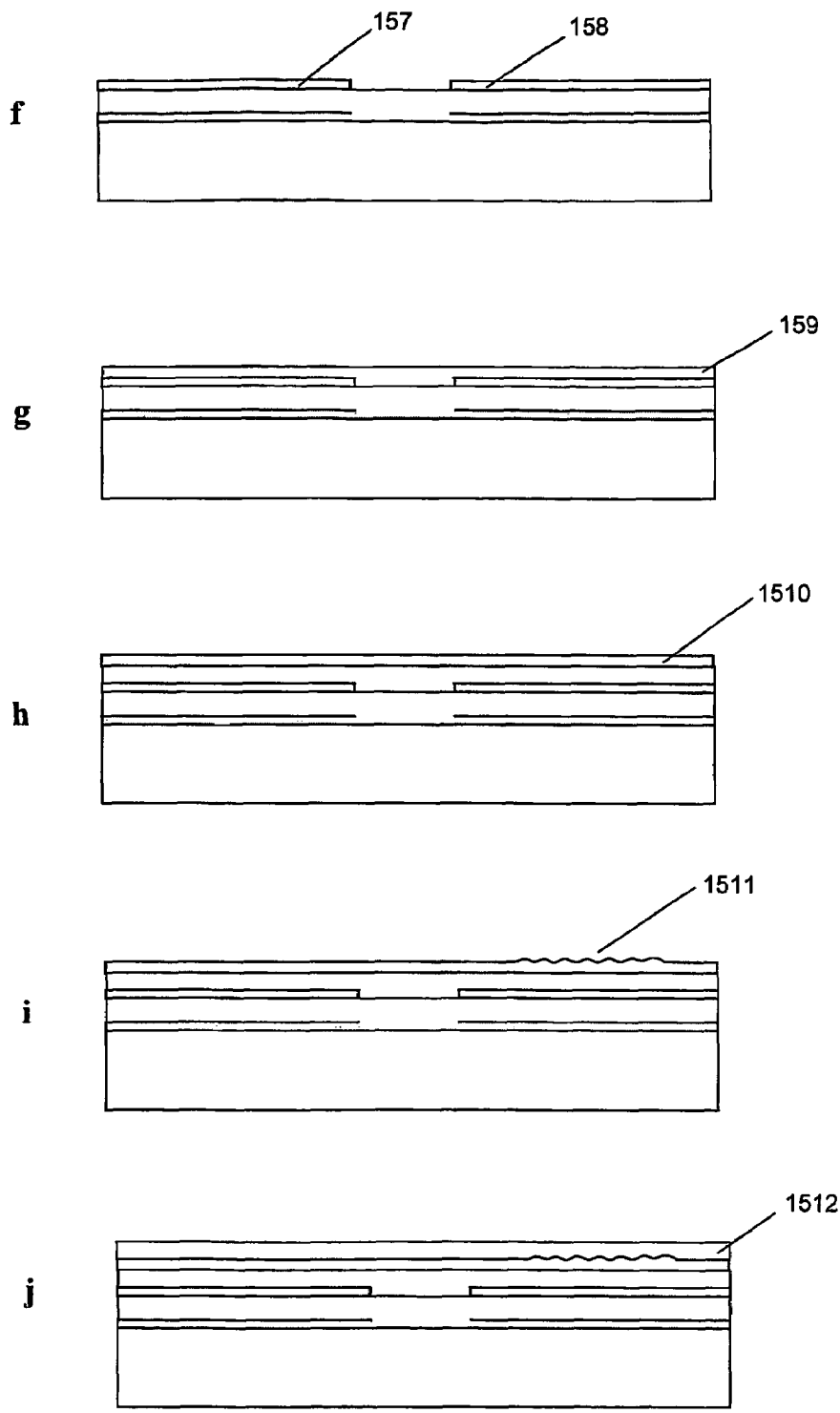
Figure 15 f-j

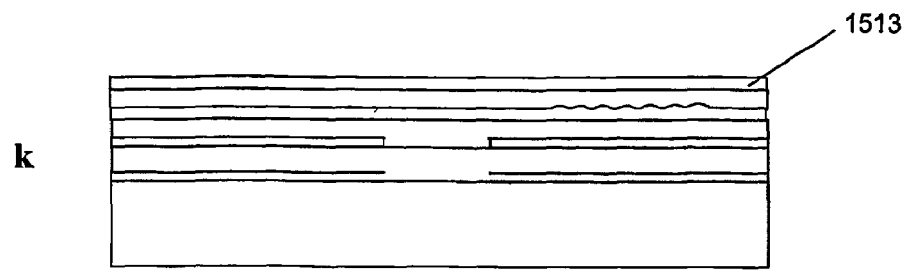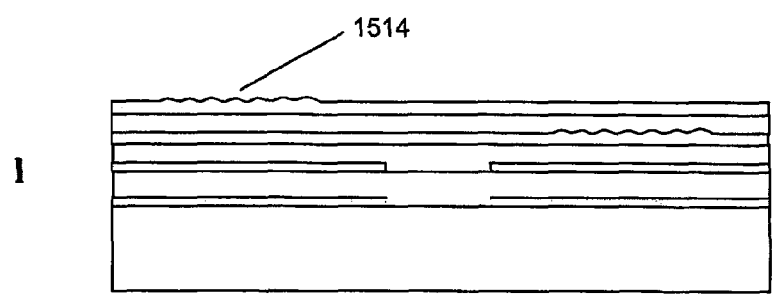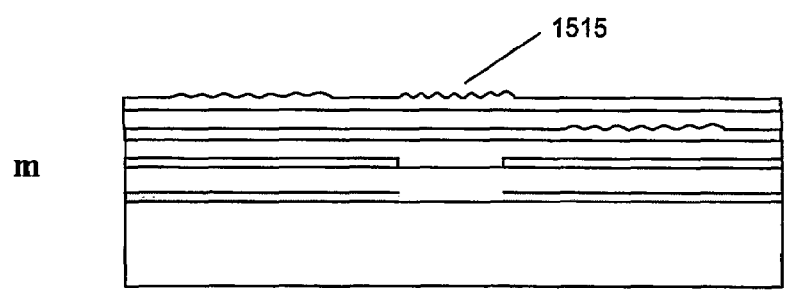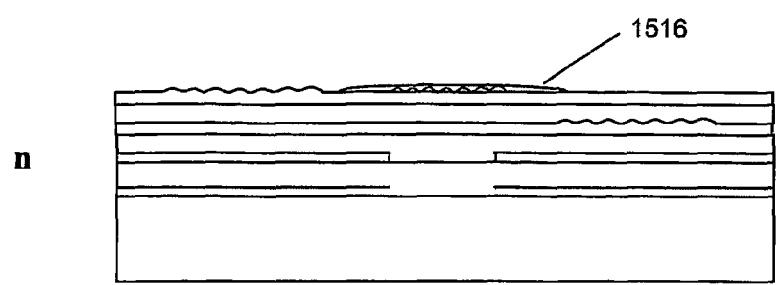
Figure 15 k-n

OPTOELECTRONIC BIOCHIP

TECHNICAL FIELD

The present invention relates to the field of biochips and in particular integrated micro-array devices for DNA and protein analysis.

BACKGROUND OF THE INVENTION

Micro-array technology for expression profiling is well known and currently is widely used in genomic research.

Over the past decade much interest has centred on the development of DNA chips based on high density oligonucleotide arrays and fluorescence analysis such as described by Hacia et al. (J. G. Hacia, L. C. Brody, M. S. Chee. S. P. A. Fodor F. S. Collins in Nature Genetics 14, Dec. 1996). One of the examples of commercialisation of this technology has been Affymetrix's "GeneChip", which was developed to process large amounts of genetic information. Affymetrix technology relies on photolithographic processing to produce thousands of binding sites on a single chip. Alternative techniques include robotic spotting and ink-jet printing although they achieve somewhat smaller binding site density within the micro-array.

For the micro-arrays in common use, one typically starts by taking a specific biological substance or system of interest, extracting its mRNA, and making a fluorescence-tagged cDNA copy of this mRNA. This tagged cDNA copy, typically called the sample probe (sometimes also called target), is then hybridised to a slide containing a grid or array of single stranded cDNA's called probes which have been built or placed in specific locations on this grid. Similar to the general hybridisation principles, a sample probe will only hybridise with its complementary probe i.e. nucleic acid strands tend to be paired to their complements in double-stranded structures. Thus, a single-stranded DNA molecule will seek out its complement in a complex mixture of DNA containing large numbers of other nucleic acid molecules. Hence, nucleic acid probe (e.g., gene probe) detection methods are very specific to DNA sequences. Factors affecting the hybridisation or reassociation of two complementary DNA strands include temperature, contact time, salt concentration, the degree of mismatch between the base pairs, and the length and concentration of the target and probe sequences. In perhaps the simplest procedure, hybridisation is performed on an immobilized probe molecule attached on a solid surface such as a nitrocellulose or nylon membrane or a glass plate.

Fluorescence is typically added to the sample probe in one of two ways: (i) fluorescent nucleotide bases are used when making the cDNA copy of the RNA or (ii) biotinylated nucleotides are first incorporated, followed by an application of fluorescence-labelled streptavidin, which will bind to biotin (I. S. Kohane "Microarrays for integrated genomics" MIT Press, 2002).

Depending on manufacturer specific protocols, the probe-sample probe (probe-target) hybridisation process on a microarray typically occurs over several hours. All unhybridised sample probes are then washed off and the micro-array is lit under laser light and scanned using laser confocal microscopy. A digital image scanner records the brightness level at each grid location on the micro-array corresponding to particular RNA species. The brightness level is correlated with the absolute amount of RNA in the original sample, and by extension, the expression level of the gene associated with this RNA.

Although term hybridisation is typically applied to DNA arrays, in this specification we will use it in a more general sense to also describe binding processes in protein arrays, e.g. binding of antigens to antibodies. It is understood that in protein arrays such binding processes occur over shorter periods of time and at lower temperatures as compared to DNA arrays.

Despite the inherent integration promise, the DNA and protein chips, while, in principle, much like the microprocessor chips that currently run today's computers, have yet to be successfully developed into monolithically integrated single chip devices that conveniently and inexpensively capture, deliver and interpret information that is gathered by what is currently known as "DNA chips" or "biochips". What is currently understood by term "biochips" is typically a glass slides with an array of binding sites, each site containing specific probe molecules, which requires complex and bulky equipment for external laser excitation, scanning and imaging of the optical signals. In addition to the cost associated with this equipment, there is also a requirement for it to be operated by highly trained and skilled personnel in order to ensure error free interpretation of the gathered data and troubleshooting. These limitations of cost and space associated with the present status of biochip technology currently prevent DNA and protein analysis from finding a wider use in hospitals and eventually in doctor surgeries.

Therefore, there is a distinct requirement for an inexpensive, disposable biochip device that could be interfaced directly to a computer and could be available to any pathology laboratory both in terms of cost and skills required to operate it. Towards that goal it would be further beneficial to simplify the DNA and protein analysis procedure by removing the need for the use of fluorescent markers in detecting specific binding events as well as by removing the washing step after the hybridisation. For research and diagnostic purposes as well as to reduce possible errors in determining a specific binding event it would be also beneficial to enable continuous monitoring of the conditions at each binding site during hybridisation. This latter feature is especially important for the protein arrays due to the relatively unstable nature of protein binding agents (as compared to DNA binding agents).

Over the past few years there has been some effort deployed to reduce cost/size of the biochips by integrating them with the associated laser excitation and image scanning apparatus (Vo-Dinh et al, "Integrated circuit biochip microsystem" U.S. Pat. No. 6,448,064, September 2002; Duveneck et al "Optical detection device based on semiconductor laser array" U.S. Pat. No. 6,469,785, October 2002; Bruno-Raimondi et al "Sensing unit provided with separated detection light guiding" U.S. Pat. No. 6,437,345, August 2002; Neuschafer et al "Sensor platform and method for the parallel detection of a plurality of analytes using evanescently excited luminescence" U.S. Pat. No. 6,078,705, June 2000). These inventions proposed an integrated circuit biochip microsystem, which combines lasers, detectors, focusing optics and biological sensing elements within a single micro-assembly. In microelectronics this type of integration is typically defined as hybrid integration i.e. when individual elements are produced separately by processing a number of separate substrates/wafers and then diced out and micro-assembled together. Although advantageous over the bulky, bench top devices, such hybrid integrated biochips still lack the cost and performance advantage of true monolithic integration. It should be further noted that all these devices require the use of fluorescent markers which unnecessarily complicates the analysis procedure and which ideally should be avoided in a simple point of care devices.

Recently, some work has been done in integration of vertical cavity surface emitting lasers (VCSELs) as light sources and photodetectors on the same III-V semiconductor substrate (GaAs) for fluorescent sensing [E. Thrush et al "Integrated biofluorescence sensor" Journal of Chromatography Vol. A1013, 2003, pp. 103-110]. Although this approach is potentially applicable to manufacturing of individual chemical or biological sensors, it does not offer a suitable technology platform for manufacturing of fully integrated disposable biochips due to inherent cost and substrate size limitations associated with III-V semiconductor compounds.

It is therefore the subject of present invention to propose a monolithically integrated biochip device, as well as a practical and cost effective method of its manufacturing. It is also a subject of the present invention to propose a biochip that can provide a lable-free detection (eliminating the need to use fluorescent markers) and in-situ monitoring of hybridisation conditions at each binding site. Using this invention a remarkable cost/performance ratio reduction can be achieved over the prior art discrete element micro-assembly devices, opening the way for the widespread use of inexpensive, disposable DNA and protein chips.

SUMMARY OF THE INVENTION

The invention in its broadest aspect comprises a biochip for testing biological substances comprising a plurality of binding sites, optical means for determining a specific binding event at each binding site, wherein the plurality of binding sites and the means for determining a specific binding event at each binding site are monolithically integrated into a single chip which is electrically powered and produces electrical signals in response to binding events at each binding site. A specific binding event at a binding site is defined as when a significant number of sample probe (or target) molecules of the biological substance under test bind to the probes present at that binding site. In the concept of the present invention a monolithically integrated chip is defined as a chip produced by processing only one substrate in a series of deposition and etching steps as opposed to hybrid integration which involves processing of a number (two or more) substrates and then aligning and attaching together the chips produced from those substrates. Another feature of monolithic integration is that all components of the chip are aligned to each other using photolithographic alignment means i.e. by reading alignment marks formed on the substrate in predetermined locations at the initial stages of the chip fabrication.

The biochip can be arranged in a way where electrical signals in response to the binding events at each binding site are induced sequentially over the entire plurality of the binding sites so that only one binding site is monitored at a time. This sequence of individual testing of the entirety of the binding sites can be repeated during hybridization process until no further changes in the conditions at the binding sites are detected. This allows for monitoring of hybridisation conditions at each binding site individually as a function of time. Such individual testing also reduces the optical crosstalk from one binding site to another as well as the general noise floor or back ground intensity level.

A monolithically integrated biochip in accordance with the present invention can be disposed of as a single device after the testing is completed thus avoiding potential risk of cross contamination which may become an issue in the prior art when certain parts of the prior art micro-assembly devices have to be reused e.g. when only the microarray part is designed to be disposable.

In the monolithically integrated biochip in accordance with the present invention the means for determining a specific binding event can comprise a plurality of light sources and a plurality of photodetectors. One light source and one photodetector can be associated with each binding site. Alternatively more than one light source and more than one photodetector can be associated with each binding site.

The biochip of the present invention can further comprise a fluidic chamber attached to the plurality of binding sites for delivering the biological substance under test. This chamber can have pumping means to flow the liquid under test along the plurality of binding sites. This fluidic chamber can also be monolithically integrated with the biochip by appropriate processing steps. In one alternative this integrated fluidic chamber can be made of the micro-imprinted polymeric layers.

In order to enable control and monitoring of conditions at each binding site the biochip can further comprise a first plurality of electrical controls for individually controlling each light source within the plurality of the light sources and a second plurality of electrical controls for individually controlling each photodetector within the plurality of the photodetectors. Such electrical controls can comprise a plurality of electrodes to deliver the drive current to the light sources and to receive electrical signals from the photodetectors. These electrodes can be implemented as multilayer metallisation with interlayer dielectric located between the metal layers located on top of each other. If required, an appropriate planarisation steps can be used to ensure a flat (planar) finished surface of the multiplayer metallisation stuck.

For a biochip comprising a plurality of light sources and a plurality of photodetectors as means for determining a specific binding event, there is a number of embodiments in which the biochip of the present invention can be realized. In the first such embodiment the biochip can be fabricated on a semiconductor (e.g. silicon) substrate and the photodetectors can be formed in that substrate. In this case the photodetectors can be formed as either a charge coupled devices (CCDs) or, alternatively, as photodiodes including avalanche photodiode. In the second embodiment the photodetectors can be realized as semiconductor thin film photodetectors and in this case a lower cost non-semiconductor substrate (e.g. glass substrate) can be used making this embodiment a more cost effective option as compared to the use of a semiconductor substrate. A semiconductor polymer can be used as a semiconductor thin film material. Alternatively, an inorganic semiconductor thin film material such as GaN or amorphous or polycrystalline silicon could be used.

Similarly to the embodiments of the present invention described above in relation to the photodetectors, the light sources can also be implemented in either a semiconductor substrate (e.g. silicon) or a semiconductor thin film. In the latter case a light emitting polymer semiconductor can be used. Alternatively, an inorganic semiconductor thin film material such as GaN or amorphous or polycrystalline silicon can be used to form a thin film light source.

In a particular embodiment of the present invention where both thin film photodetectors and thin film light sources are used, a further advantageous alternative from the manufacturing cost point of view can be realised when both light sources and photodetectors are formed in the same semiconductor thin film p-n bi-layer based on the principle of the light source/photodetector performance reciprocity [M. A. Green et al "Efficient silicon light-emitting diodes" Nature, Vol. 412, 2001, pp. 805-808]. The same processing steps can be used to form electrodes for both light sources and photodetectors further reducing the manufacturing costs. Another advantage of this embodiment is a substantially planar surface of the integrated light source/photodetector structure due to eliminating the need for a number etch-off and deposition steps, which typically result in a significant surface topology.

The wavelength of light emitted by the thin film light sources and the wavelength of light preferentially received by the thin film photodetectors can be controlled by arranging the light sources and the photodetectors in the form of micro-cavity devices where the dimension of the resonant cavity in which the semiconductor material is enclosed, is in the order of wavelength of light to be emitted or detected, respectively [H. Yokoyama "Physics and device applications of optical microcavities" Science, Vol. 256, April 1992, pp. 66-70]. Placing the semiconductor layer between two mirrors can form a vertical micro-cavity. The two electrodes of light source/photodetector can be used as the mirrors. Alternatively, a micro-cavity can be produced by forming a photonic band gap micro-cavity [P. Bhattacharya "Cavities of crystal light" IEEE Circuit and Devices Magazine, March 2003, pp. 25-33] through an appropriate periodic structure incorporated in the semiconductor layer. The resonant wavelength of such photonic band gap micro-cavity can be adjusted by adjusting the photonic band gap design. The advantage of this photonic band gap micro-cavity embodiment is that more than one wavelength for the light sources and more than one wavelength for the photodetectors that can be defined in a single lithographic step. For the case of a vertical micro-cavity such multi-wavelength definition will require a number of etching steps to locally adjust the cavity dimension i.e. the thickness of the semiconductor p-n bi-layer.

Among optical techniques for determining a specific binding event the planar waveguide evanescent field excitation method [W. Lukosz "Integrated optical chemical and direct biochemical sensors" Sensor and Actuators Vol. B29, 1995, pp. 37-50; G. L. Duveneck et al "Planar waveguides for ultra-high sensitivity of the analysis of nucleic acids" Analytica Chimica Acta Vol. 469, 2002, pp. 49-61.] has the advantage of minimizing bulk scattering and improving signal to noise ratio. Another advantage of this method is the possibility to avoid washing step after hybridization since the light interact only with bound probe-target molecules that are close to the waveguide surface.

Within the concept of the present invention such waveguide is monolithically integrated with the light sources and the photodetectors. The binding site is formed on the surface of the waveguide so that the evanescent field of light propagating in the waveguide interacts with the biological substance under test. This planar waveguide can be made of high refractive index inorganic material such as tantalum oxide or titanium oxide. Alternatively the waveguide can be made of organic material such as optically transparent polymer. The latter option is typically more cost effective and also allows for using embossing techniques to create micropatterns, such as gratings or photonic band gap structures, in the soft polymeric waveguide material.

To couple light into the waveguide from a light source and to decouple light from the waveguide onto a photodetector one or more diffraction gratings can be used. Such grating could be a corrugation grating located at the top or at the bottom of the waveguide layer. Alternatively, such grating could be located in the vicinity of the waveguide layer. More than one diffraction grating can be used to improve incoupling/outcoupling efficiency. For example, two gratings could be used for each incoupling/outcoupling function. In this configuration the purpose of the first grating is to diffract light towards the second grating at an angle that improves the overall incoupling/outcoupling efficiency.

In an alternative embodiment the waveguide incoupling and outcoupling can be achieved by way of a tilted mirror located in or in the vicinity of the waveguide. Such tilted mirror can be fabricated as an angled metalised facet etched into the waveguide.

In some biochip applications the use of more than one type of fluorescent markers is required. In this context another embodiment of the biochip in accordance with the present invention allows for testing biological substance marked with one or more fluorescent markers. In such biochip there is more than one light source associated with each binding site and/or more than one detector associated with each binding site. The light sources and/or photodetectors associated with each binding site can operate at different wavelengths. The light sources are tuned to the excitation wavelengths of the corresponding fluorescent markers and the detectors are tuned to the emission wavelength of the corresponding fluorescent markers. The wavelength tuning can be achieved for example by adjusting the micro-cavities of the respective light sources and photodiodes as was described earlier.

Another embodiment of the present invention proposes the use of absorption markers as opposed to fluorescent markers. According to this embodiment the absorption markers are attached to the molecules of the biological substance under test and the means for determining a binding event at each site comprise means for determining a change in absorption associated with the binding event. More then one type of absorption markers with absorption bands at different wavelengths could be used. The evanescent field of the light propagating in the waveguide interacts with the absorption markers attached to target molecules hybridized at the binding site, which causes reduction in intensity of light transmitted through the waveguide proportional to the amount of the bound molecules on its surface. This reduction in intensity is received by a photodetector and used to determine a specific binding event at the site.

It is generally beneficial to eliminate the need for the use of markers in determining a specific binding event. Such marker-free binding event recognition can be achieved by registering a change in refractive index resulting from a specific binding. The evanescent field of the waveguide interacting with a layer of bound molecules changes the effective refractive index or propagation constant of the optical mode of the waveguide. A number of embodiments of the present invention detect such change in refractive index associated with the specific binding event by translating it into a change in the light intensity decoupled from the waveguide onto the photodetector. One such embodiment uses a grating assisted vertical coupler structure. The structure comprises a first planar waveguide on surface of which the binding event takes place, a grating formed in said waveguide and extending across the binding site, a second planar waveguide located below the first waveguide and separated by a coupling layer of lower refractive index than that of the two waveguides. The parameters of the grating, first and second waveguides and the coupling layer are selected such that the amount of light coupled from the first waveguide into the second waveguide changes in response to a binding event on the surface of the grating formed in the first waveguide. Alternatively, a structure of a simple vertical coupler (i.e. without grating) could be used where the parameters of the two waveguides and the coupling layer are selected such that the amount of light coupled from the first waveguide into the second waveguide changes in response to a binding event on the surface of the first waveguide.

Surface plasmon resonance technique can also be used for lable-free detection [A. Hanning, U.S. Pat. No. 5,641,640, June 1997], especially as applied to protein biochips. In this case a thin metal layer (typically gold) can be deposited on the surface of the waveguide and the binding sites are then formed on this metal layer. A refractive index change resulting from a binding event occurring on the surface the metal layer will shift the wavelength of the plasmon absorption peak and in turn will change the intensity of light transmitted through the waveguide as detected by the photodetector. The wavelength of the light source can be selected so that by increasing the drive current of the source its emission wavelength sweeps across the plasmon absorption peak to register the change in the peak position resulting from a binding event.

To enable in-situ monitoring of the status of hybridization at each binding site as a function of hybridisation temperature, each site could further contain a reference waveguide path which is identical to the one used to monitor binding events but which does not have probe molecules formed on its surface. By using this reference waveguide path a change in refractive index resulting from a change in the temperature of the site or the temperature of the chip as a whole could be separated from the change in refractive index resulting from a specific binding event.

To better utilize the light emitted by a light source it can be shared between a number of binding sites including additional reference waveguide paths a described above. In this instance the binding sites and the reference waveguide paths can be arranged symmetrically around the light source.

In some applications the probes located on different binding sites within the plurality of binding sites (microarray) require different hybridization conditions. Therefore, a further embodiment of the present invention proposes a biochip with a plurality of electrodes to control hybridization conditions at each binding site. Such electrodes could be arranged in a number of layers via multilevel metallisation approach and could be incorporated into the structure during the fabrication. The electrodes could be used to apply voltage to binding sites to enhance hybridization or/and to remove non-specifically bound molecules e.g. via application of electric field. If the electrodes are arranged in the form a thin film heaters, the current driven through these electrodes can be used to control hybridization temperature individually at each binding site.

In order to facilitate control of each binding site one or more transistors could be formed at each binding site. If silicon substrate is used such transistors can be made using CMOS technology. Alternatively, these transistors can be formed as a thin film transistors, e.g. in amorphous silicon, and incorporated in the biochip structure.

In all relevant embodiments of the present invention the intensity of light emitted by the light sources can be modulated at a certain frequency and this frequency can then be filtered out from the corresponding photodetector signal in order to improve signal to noise ratio at each binding site. Additionally, when fluorescent markers are used, such modulation can provide information about the characteristic fluorescent decay time which in turn can provide additional information about the hybridization process.

In a second aspect of the present invention there is provided a method of manufacturing a biochip comprising steps of forming binding sites, light sources and photodetectors as well as any auxiliary means for determining a specific binding event, wherein said light sources, photodetectors, binding sites and auxiliary means for determining a specific binding event are produced by processing a single planar substrate in a sequence of etching and deposition steps. In this method the light sources, detectors, binding sites and any auxiliary means for determining a specific binding event are photolithographically aligned to each other. The method can further comprise steps of (i) forming a first plurality of electrodes that are optically non-transparent; (ii) forming at least one semiconductor p-n bi-layer layer; (iii) forming a second plurality of electrodes which are optically transparent; (iv) forming at least one planar waveguide layer; (v) forming means of light in- and out-coupling for the waveguide layer; and (vi) forming a plurality of binding sites on the surface of the waveguide layer. The individual biochips are then diced out from the substrate and are wire-bonded into packages. The entire packaged biochip could be disposed after use.

In a third aspect of the present invention there is provided a method of testing a biological substance comprising steps of disposing the substance over a plurality of binding sites, hybridization of the substance to the binding sites and detection the occurrences of binding events at each site, said method further comprising the use of a single disposable biochip which is electrically powered and produces electrical signals in response to binding events at each binding site. The method can advantageously allow for individual monitoring of the conditions at each binding site during the hybridization. Such monitoring can comprise generation an optical signal sequentially at each binding site, interaction of the optical signal with the biological substance, conversion of optical signal into electrical signal, said electrical signal containing information about the status of hybridization at each binding site. This information can be derived from a change in refractive index, or from a change in intensity of light emitted by fluorescent markers, or from a change in attenuation induced by absorption markers.

A further advantageous feature of this method is that all binding sites prior to the disposing the biological substance can undergo individual testing. The testing data could then be stored and used for interpretation of the information received from the corresponding binding sites during hybridization in order to reduce error in determining a specific binding event. In the testing and monitoring process the input optical signal sent at each binding site can be modulated at a certain frequency and the electrical output signal can then be filtered out at that frequency to improve signal to noise ratio.

It is to be understood that, if any prior art publication is referred to herein, such reference does not constitute an admission that the publication forms a part of the common general knowledge in the art, in Australia or any other country.

For the purposes of this specification it is to be understood that the word "comprising" means "including but not limited to", and that the word "comprises" has a corresponding meaning.

BRIEF DESCRIPTION OF THE DRAWINGS

Embodiments of invention will now be described, by way of example only, with reference to accompanying drawings.

FIG. 15a-n illustrates a method of manufacturing of a biochip in accordance with the second aspect of the present invention.

DETAILED DESCRIPTION OF THE DRAWINGS

Figure 1:
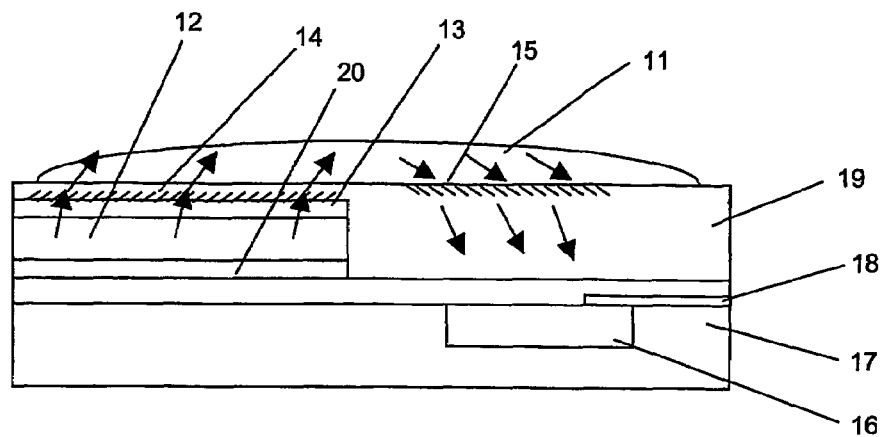
FIG. 1 illustrates a cross-section of first embodiment of the biochip in accordance with present invention utilising a thin film light source and a photodetector in a semiconductor substrate.

Turning to FIG. 1, there is shown a cross-section of first embodiment of the biochip in accordance with present invention utilising a thin film light source and a photodetector in a semiconductor substrate. Light is emitted by a thin film light source comprising a semiconductor p-n bilayer 12, passes through a transparent top electrode 13 and is refracted towards biological substance under test 11 by a diffraction grating 14. The biological substance 11 can be disposed in the form of a gel. The luminescence exited in the biological substance by the incident light is then refracted onto a photodetector 16 by a second diffraction grating 15. The period of the diffraction grating is chosen to diffract the wavelength of luminescent light as opposed to the wavelength of excitation light. The rejection of the excitation light relative to the luminescent light can be further enhanced by a band pass thin film filter (not shown in FIG. 1) that can be formed on the surface of the photodetector 16.

Semiconductor substrate can be made of silicon and the photodetector can be implemented using known processing techniques in either photodiode or charge coupled device (CCD) configurations as described for example in [M. L Adams et al "Microfluidic integration on detector arrays for absorption and fluorescence micro-spectrometers" Sensor and Actuators, Vol. A104, 2003, pp. 25-31]. The thin film light source can be implemented as an organic light emitting diode utilising processing techniques described in [L. S. Hung et al "Recent progress of molecular organic electroluminescent material and devices" Material Science and Engineering Vol. R39, 2002, pp. 143-222]. Top transparent electrode can be made of indium tin oxide (ITO) deposited by known techniques such as electron beam evaporation or sputtering. A layer 19 is used to planarise surface topology created after definition of the light source areas and opening the photodetector areas. It can be made as a span-on silica sol-gel or polyimide layers. The diffraction grating 14 used to refract light emitted by the organic light emitting diode can be realised in either the ITO electrode 13 or the planarisation layer 19 by means of holographic exposure of a layer of photoresist and subsequent etching. Alternatively, the grating can be formed by embossing a hard micro-structured stamp into a soft polymeric material. The light source 12 is operated by applying voltage between electrodes 20 and 13, while the photodetector is operated by applying voltage between electrode 16 and the substrate 17.

Figure 2:
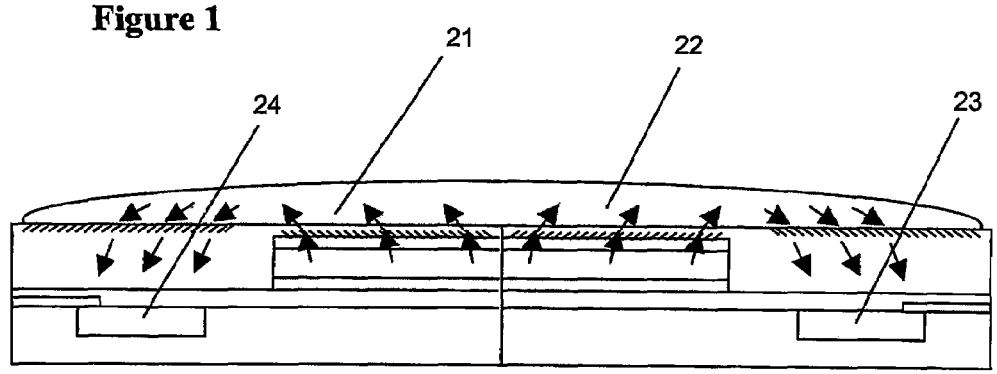
FIG. 2 illustrates a cross-section of second embodiment of the biochip in accordance with present invention which is based on the first embodiment but utilising a bidirectional thin film light source.

In FIG. 2 the same concept as described above in relation to FIG. 1 is extended to provide for the light emitted from the light source to be diffracted in both directions 21, 22 and for the luminescence to be received by two photodetectors 23 and 24. This structure in addition to better utilising the light emitted by a single light source is also better suited for implementation of an interdigital structure described in relation to FIG. 3.

Figure 3:
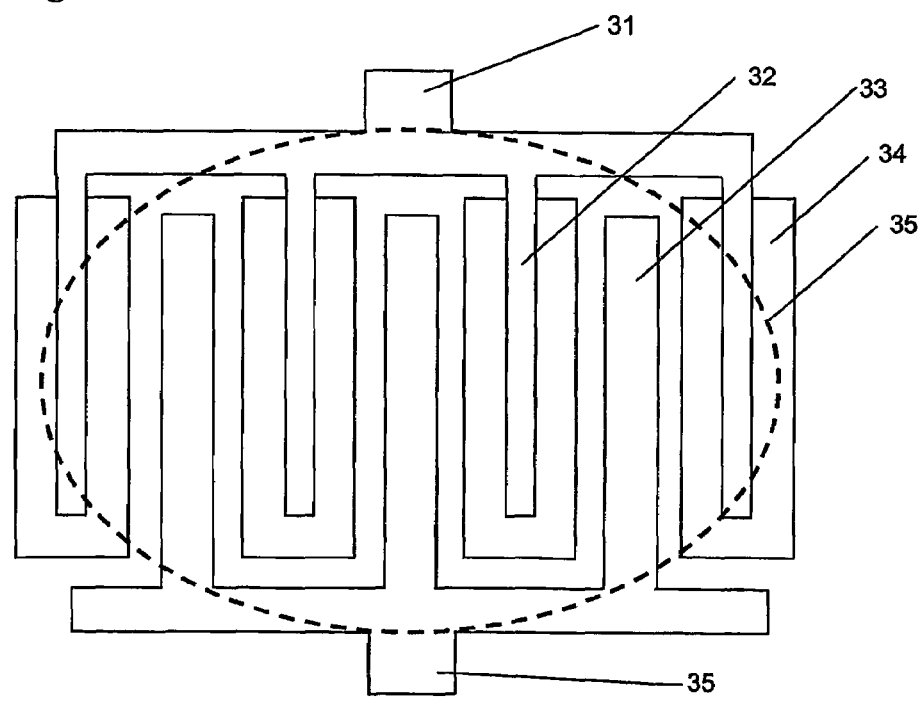
FIG. 3 illustrates a top view of the second embodiment of the biochip in accordance with present invention, which utilises an interdigital configuration of the light sources and photodetectors.

FIG. 3 shows an interdigital configuration of light sources and photodetectors. Since the light emitted close to the junction between the light source and the photodetector generates most of the luminescence received by the photodetector, such configuration allows for better utilisation of the emitted light. As shown in FIG. 3 the electrodes associated with light sources 33 and photodetectors 32 within a single binding site 35 are made in the form of interdigital combs, each comb connected to the same driving electrodes 31, 35 extending to the periphery of the biochip.

Figure 4:
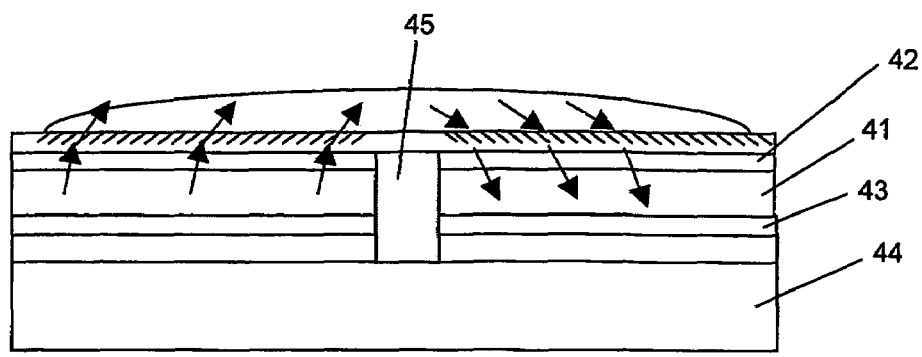
FIG. 4 illustrates a cross-section of third embodiment of the biochip in accordance with present invention utilising a thin film light source and a thin film photodetector.

FIG. 4 shows a cross section of a biochip similar to that described in relation to FIG. 1 but where the photodetector is realised in a thin film form as opposed to be made in a semiconductor substrate. Such photodetector consists of semiconductor p-n bi-layer 41 bottom electrode 43 and top electrode 42 and could be realised in a semiconductor polymer material as described in [K. S. Narayan et al "Novel strategies for polymer based light sensors" Thin Solid Films Vol. 417, 2002, pp. 75-77]. The photodetector semiconductor bi-layer can be formed separately from the light source semiconductor bi-layer. Alternatively, due to light source/photodetector reciprocity, the photodetector could be fabricated in the same semiconductor polymer layer as the light source. In this latter case the light source and detector areas can be simply formed by the photolithographic definition of the top and bottom electrodes. The advantage of this alternative is a significantly simplified fabrication procedure and the corresponding reduction in biochip manufacturing costs. A low cost glass or ceramic substrate 44 can be used. To overcome a potential electrical or optical cross talk problems an isolation groove 45, as shown in FIG. 4, can be used. For optical isolation the grove can be filled with a light absorbing material.

In the previously described embodiments the control of the wavelength emitted by the light source can be achieved by employing a vertical cavity light sources in which the cavity design determines the emitted wavelength [F. Jean et al "Microcavity organic light-emitting diodes on silicon" Applied Physics Letters, Vol. 81, 2002, pp. 1717-1719; T. Shiga et al "Design of multiwavelength resonant cavities for white organic light-emitting diodes" Journal of Applied Physics, Vol. 93, pp. 19-22]. Similarly, a vertical cavity photodetectors can be tuned to a certain wavelength by appropriate cavity design. In the case when the biological substance under test is marked with fluorescence markers the light source is tuned to the excitation wavelength of the fluorescent markers and the photodetector is tuned to emission wavelength of the fluorescent markers. In the instance where more than one fluorescent marker are used the corresponding number of the light sources and photodetectors can be associated with the one binding site and each additional source/detector pair tuned to the excitation/emission wavelength of each additional fluorescent marker used at this binding site.

Figure 5:
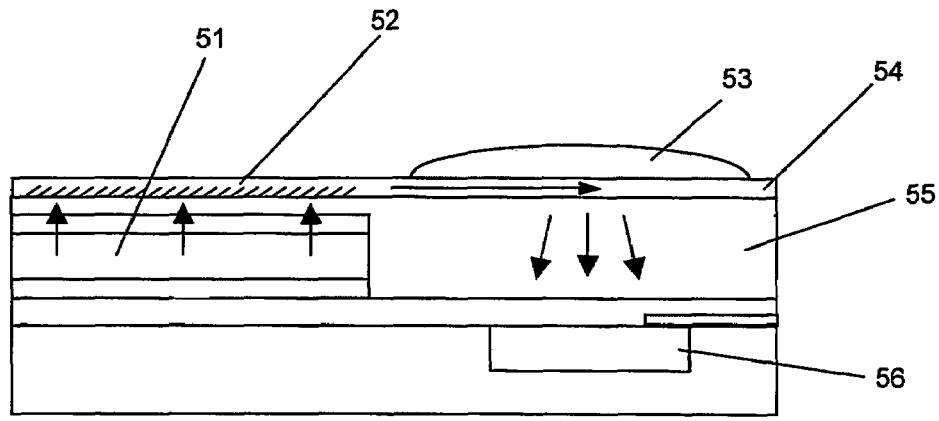
FIG. 5 illustrates a cross-section of forth embodiment of the biochip in accordance with present invention utilising a thin film light source and a photodetector in a semiconductor substrate and a waveguide for evanescent field excitation.

FIG. 5 shows an embodiment of the present invention where the biological substance under test is excited by an evanescent field of a planar waveguide the surface of which forms a binding site. The light emitted by a thin film light sources 51 is redirected and launched into a planar waveguide 54 by a diffraction grating 52. The luminescent emission induced in biological substance 53 by the evanescent field of the waveguide is collected by a photodetector 56 fabricated in a semiconductor substrate. The waveguide can be formed for example by electron beam evaporation and can be made of high refractive index optically transparent material such as titanium oxide or tantalum oxide. The thickness of the waveguide is selected for it to support a single transverse optical mode at the wavelength emitted by the light source, typically 150 nm for tantalum oxide waveguide. There could be a thin film filter formed on the surface of the photodetector (not shown) to filter out the luminescent signal from the excitation signal.

Figure 6:
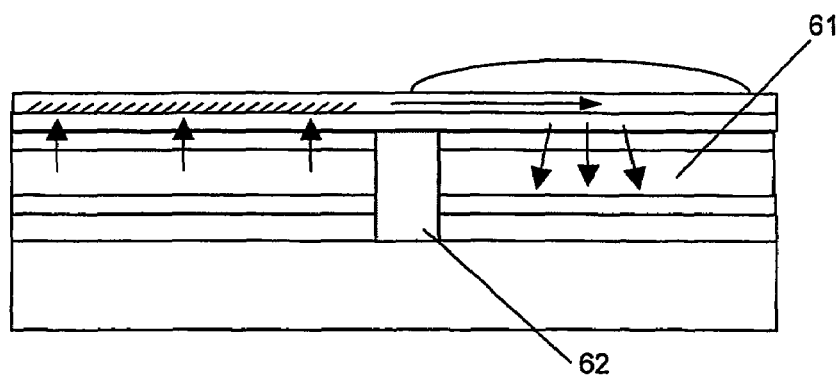
FIG. 6 illustrates a cross-section of fifth embodiment of the biochip in accordance with present invention utilising a thin film light source and a thin film photodetector and a waveguide for evanescent field excitation.

FIG. 6 shows a conceptually similar embodiment to that shown in FIG. 5 with the difference being that the photodetector 61 is formed in a thin film form. An optical isolation trench 62 could be used to reduce unwanted optical cross-talk between the source and the detector. The wavelength selectivity of the photodetector 61 can be achieved by either employing a thin film filter as described in relation to FIG. 5 or by using a vertical micro-cavity photodiode with the resonant wavelength of the cavity tuned to the luminescence emission wavelength.

Figure 7:
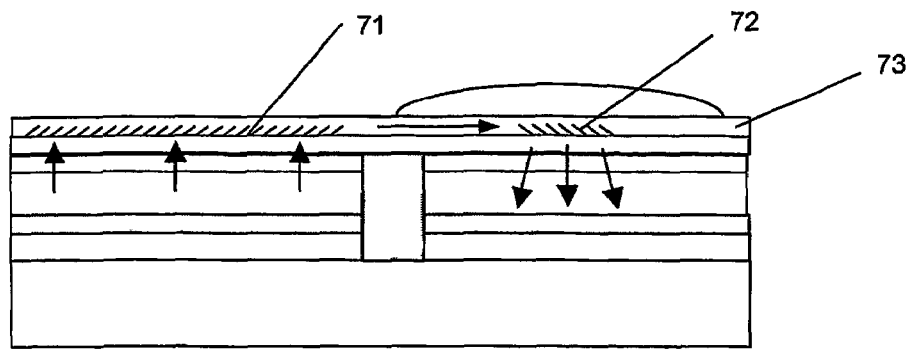
FIG. 7 illustrates a cross-section of sixth embodiment of the biochip in accordance with present invention utilising a thin film light source and a thin film photodetector, a waveguide for evanescent field excitation and a grating to decouple luminescent signal onto the photodetector.

The biochip embodiment shown in FIGS. 7 is used to determine a specific binding events using absorption markers as opposed to the use of fluorescent markers that were described in relation to FIGS. 5 and. 6. The light emitted by the light source is refracted and launched into the planar waveguide 73 by diffraction grating 71. The evanescent field of the waveguide mode interacts with biological substance on its surface and experiences different degree of attenuation depending on the amount of absorption centres present in the biological substance. A fraction of light is then refracted onto the photodetector by the second diffraction grating 72. In principle the absorption band of the fluorescent markers can be used in this case. Before the binding event takes place the light source/detector pair is activated to record a background absorption level. Then after the biological substance is disposed over the binding site and hybridisation is induced, the absorption is measured again and compared to the background level to determine whether a specific binding event took place. The light source has to be tuned to the absorption band of the markers, eg by using appropriate vertical microcavity, while the photodetector can be non-wavelength specific.

Figure 8:
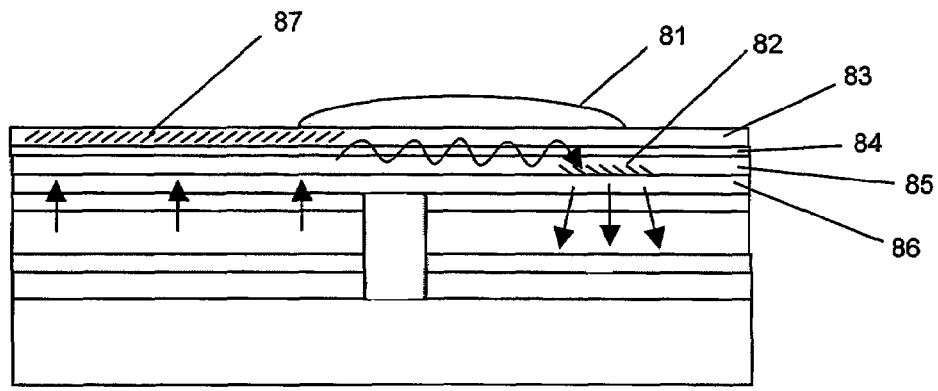
FIG. 8 illustrates a cross-section of seventh embodiment of the biochip in accordance with present invention utilising a thin film light source, a thin film photodetector and a waveguide for evanescent field excitation formed as a part of a vertical coupler.

FIG. 8 shows an embodiment of the present invention where the binding event could be determined without the use of florescent or absorption markers by way of detecting a change in refractive index associated with the binding event. This is done by using a vertical coupler consisting of a first planar waveguide 85, a coupling layer of lower refractive index 84 and a second planar waveguide 83. The light is coupled into the second waveguide via a first diffraction grating 87, and while propagating in the second waveguide, is being coupled into the first waveguide. The degree of coupling depends on the effective refractive index of the optical mode propagating in the first and second waveguides. The latter in turn depends on the refractive index of the biological substance present on its surface. When a specific binding event takes place the refractive index of the biological substance changes which causes a change in the amount of light coupled from the second waveguide into the first waveguide. In turn this causes a change in amount of light refracted out of the first waveguide onto the photodetector by the second grating 82. As in the previous embodiment, the amount of light received by the detector is normalised by activating the light source/detectors pairs before the biological substance is disposed over the binding site.

Figure 9:
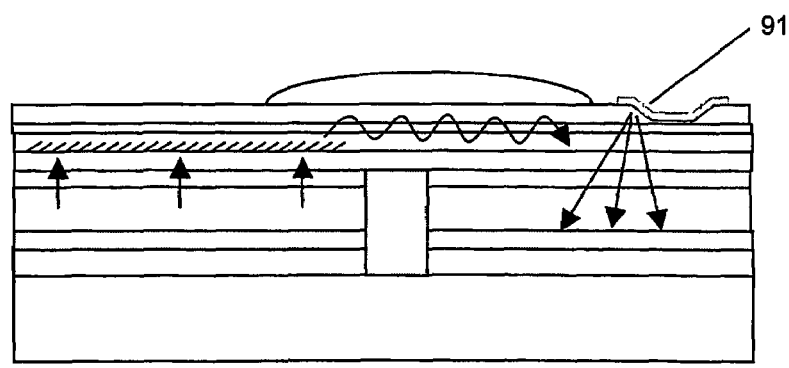
FIG. 9 illustrates a cross-section of eighth embodiment of the biochip in accordance with present invention utilising a thin film light source and a thin film photodetector and a waveguide for evanescent field excitation formed as a part of a vertical coupler with a metallised mirror for light defection onto a photodetector.

FIG. 9 illustrates a similar embodiment to that described in relation to FIG. 8 with exception that a tilted metallised mirror 91, as opposed to the grating, is used to decouple the light from the second waveguide. In this case a larger fraction of light can be decoupled from the waveguide and launched onto photodetector and, therefore, greater sensitivity of the light source/detector pair can be achieved.

Figure 10:
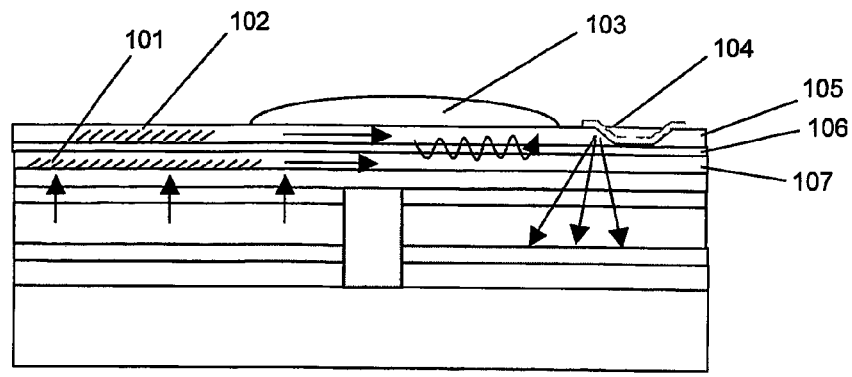
FIG. 10 illustrates a cross-section of nineth embodiment of the biochip in accordance with present invention utilising a thin film light source and a thin film photodetector and a waveguide for evanescent field excitation formed as a part of a vertical coupler in which light is simultaneously launched into the two waveguides.

FIG. 10 shows another embodiment of the present invention where the specific binding event can be determined by means of detecting a refractive index change associated with the binding event. The device employs a vertical coupler consisting of first planar waveguide 107, a lower refractive index coupling layer 106 and a second planar waveguide 105. The light emitting by the light source is launched simultaneously into the first and second waveguides by the diffraction gratings 101 and 102 respectively. Optical modes propagate in the first and second waveguides and interact with each other creating an interference pattern. This interference pattern depends on the effective refractive index of the optical mode propagating in the second waveguide which in turn depends on the refractive index of the biological substance on its surface via the evanescent field interaction. The change in refractive index of the biological substance associated with the binding event causes the interference pattern to shift and the intensity of light reflected by the tilted mirror 104 towards photodetector changes accordingly. The sensitivity of the interference pattern to the change in refractive index can be adjusted by adjusting the thickness and refractive index of the coupling layer. Prior to disposing the biological substance the source/vertical coupler/detector system has to be calibrated to record the reference signal.

Figure 11:
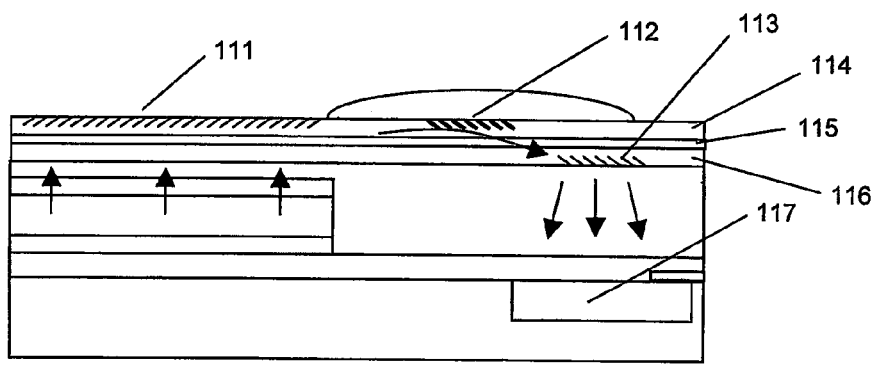
FIG. 11 illustrates a cross-section of tenth embodiment of the biochip in accordance with present invention utilising a thin film light source, a photodetector in a semiconductor substrate and a waveguide for evanescent field excitation arranged as a part of a grating assisted vertical coupler.

FIG. 11 illustrates a cross section of yet another embodiment of the present invention that detects refractive index change associated with a specific binding event. The device uses a grating assisted vertical coupler consisting of a first planar waveguide 116, a coupling layer of lower refractive index 115 and a second planar waveguide 114; it also includes a grating 112 formed in the second planar waveguide. The light is coupled into the second planar waveguide via a diffraction grating 111 and propagates towards grating 112. Grating 112 is designed to assist coupling of light from the second to the first waveguide with the fraction of coupled light depending on the average refractive index of the grating which, in turn, depends on the refractive index of the biological substance disposed over the grating. The coupled light is then deflected onto photodetector 117 by a diffraction grating 113. Alternatively the light can be reflected by a tilted mirror formed in the second waveguide as described in relation to FIG. 10.

Figure 12:
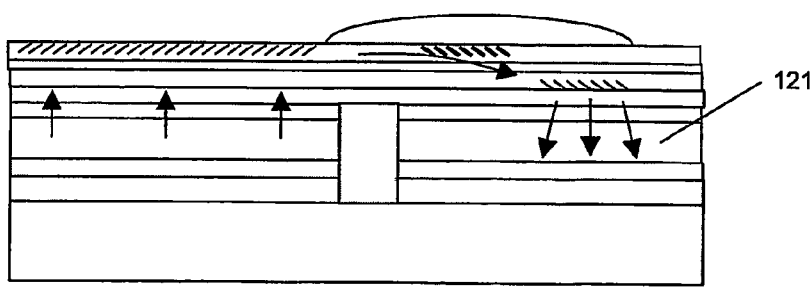
FIG. 12 illustrates a cross-section of eleventh embodiment of the biochip in accordance with present invention utilising a thin film light source, a thin film photodetector and a waveguide for evanescent field excitation arranged as a part of a grating assisted vertical coupler.

FIG. 12 illustrates an embodiment of the present invention that is similar to that described in relation to FIG. 11, but uses a thin film photodetector 121 as opposed to a photodetector formed in semiconductor substrate 117. While having somewhat smaller sensitivity as compared to the semiconductor substrate detector, the thin film photodetector allows for significant reduction in the biochip manufacturing costs. Its use, therefore, can be determined by the balance of cost/performance in relation to a particular application.

Figure 13:
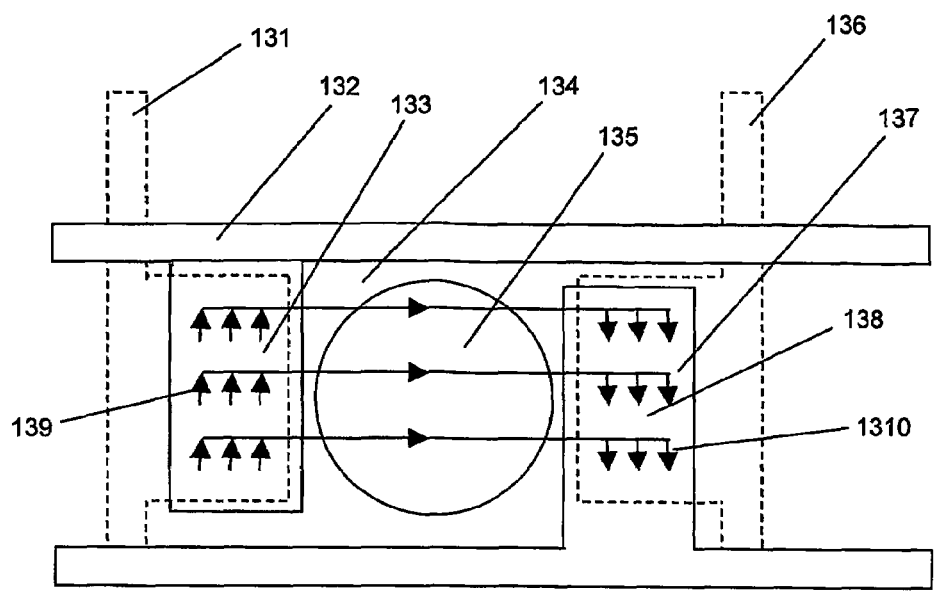
FIG. 13 illustrates a top view of a general embodiment of the biochip in accordance with present invention utilising planar waveguide evanescent optical field excitation or interaction.

FIG. 13 illustrates a top view of a thin film light source/photodetector pair connected by a waveguide and associated with each binding site of the plurality of binding sites in accordance with present invention. It consists of bottom 131 and a transparent top 132 electrodes of the thin film light source, one of the planar waveguide configurations as described above comprising at least one planar waveguide 134, a binding site 135 formed on the surface of the waveguide, a means 139 for coupling light from the light source into the waveguide and means 1310 for decoupling light from the waveguide onto a thin photodetector 138 comprising a transparent top electrode 137 and bottom electrode 136. The light emitted by the thin film light source is coupled into the waveguide where the evanescent field of the waveguide mode interacts with the biological substance 135 and is then decoupled from the waveguide and received by a thin film photodetector.

Figure 13A:
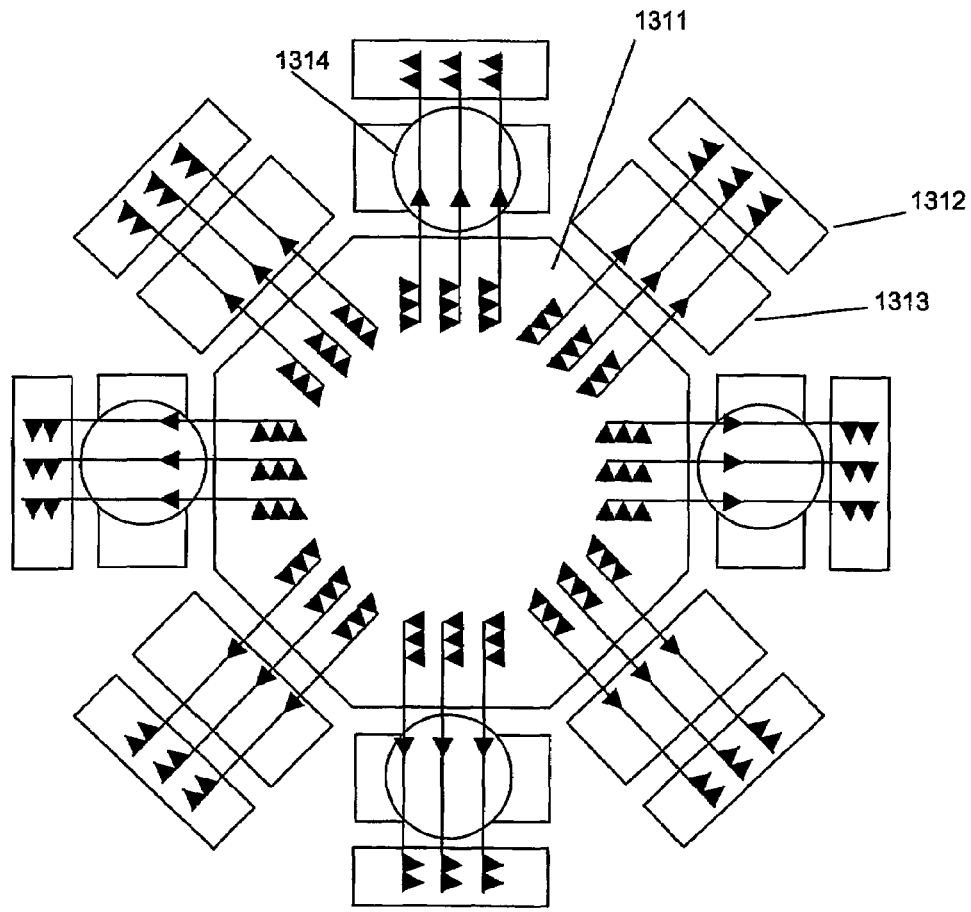
FIG. 13a illustrates a top view of another embodiment of the biochip in accordance with present invention utilising planar waveguide and a light source sharing scheme with reference paths.

FIG. 13 illustrates a top view of another alternative of a thin film light source/photodetector arrangement where one light source 1311 is shared between 8 waveguide 1313/photodetector 1312 pairs. This arrangement contains 4 binding sites 1314 formed on top of 4 out of 8 waveguides whereas 4 remaining waveguides act as reference paths. These reference paths are required to enable separation of refractive index changes associated with binding events at the binding sites and refractive index changes due to temperature changes during hybridisation. Such reference paths allow for continuous monitoring of the hybridisation state at different sites as the temperature of the chip is ramped up and enables determination of sites with non-specific binding which tend to decouple above certain characteristic temperature whereas specifically bound molecules remain bound above this temperature. This light source sharing arrangement with reference paths also allows to remove any instability in the light source operation as a potential cause for an error in detecting a binding event. It is understood that the pattern depicted in FIG. 13a can be replicated in a 2D array and wiring can be provided to the light sources and photodetectors in the form of transparent top and non-transparent bottom electrodes.

Figure 14:
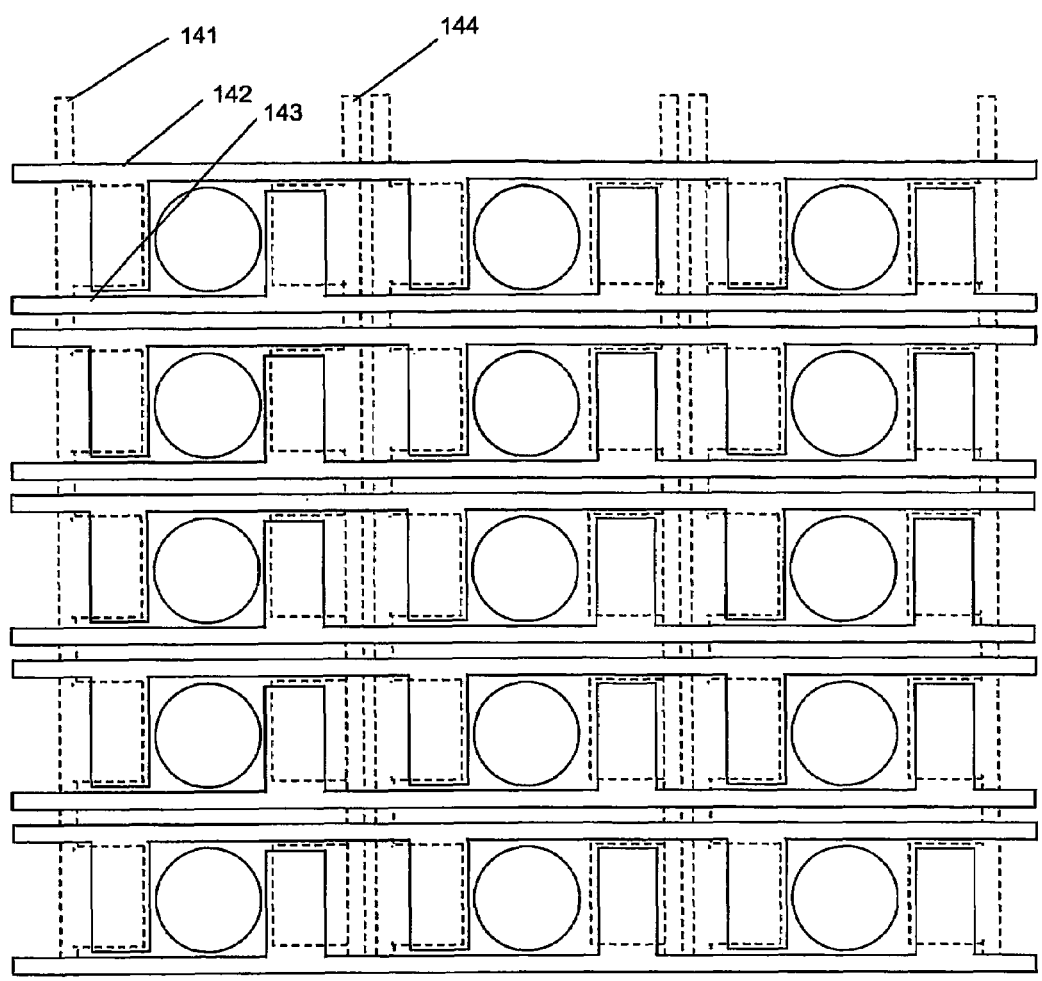
FIG. 14 illustrates a layout of a plurality of binding sites with associated means for determining a binding event at each site.

FIG. 14 illustrates a layout of an embodiment of a biochip in accordance with the present invention. It consists of a plurality of binding sites and a thin film light source/detector pair associated with each binding site. The biochip is arranged in rows and columns. Each raw shares a common top electrode 142 of the light source and a common top electrode of the photodetector 143. Each column shares a common bottom electrode 141 of the light source and a common bottom electrode 144 of the photodetector. By applying signal to the appropriate rows and columns one light source/photodetector pair can be activated at a time.

FIGS. 15a-l illustrate an embodiment of a method of manufacturing a biochip in accordance with a second aspect of the present invention. The biochip shown in this embodiment comprises, at each binding site, a thin film light source and a thin film detector and a grating assisted vertical waveguide coupler for determining a specific binding event in a marker-free biological substance by way of detecting the refractive index change.

A glass substrate 151 with an optical quality finish is first chemically treated to remove any dust or residues from it surface. A layer of a bottom electrode metal 152 such as aluminium is then evaporated or sputtered on the glass substrate (FIG. 15b). The thickness of the aluminium layer is determined by the size of the biochip and the corresponding length of the raw and column electrodes such that the necessary conductivity is achieved. The aluminium layer is then patterned by photolithography and etching (FIG. 15c) to produce pattern of bottom electrodes for the light sources 153 and for the photodetectors 154 which are arranged in rows and columns as illustrated in FIG. 14. A semiconductor small molecule organic p-n bi-layer 155 e.g. 75 nm of TPD and 75 nm of Alq3 is then evaporated on the surface (FIG. 15d). Alternatively, a polymer semiconductor p-n bi-layer such as described in [J. H Burroughes et al "Light emitting diodes based on conjugated polymers" Nature Vol. 347, 1990, pp. 539-541] can be spin coated on the surface of the bottom electrode. In this latter case the surface topology created by patterning of the bottom electrodes is fully or partially planarised. Thus formed semiconductor bi-layer will subsequently be used for formation of both light sources and photodetectors. A top transparent electrode conductive layer such as ITO is then sputtered or evaporated on top of the semiconductor bi-layer (FIG. 15e) and patterned to form rows and columns of the top electrodes of light sources 157 and photodetectors 158 (FIG. 15f). A separation and planarising layer 159 such as optically transparent polyimide is then span on top metallisation. The purpose of this layer is to create planar surface for the subsequent formation of the planar waveguide and to optically isolate the waveguide from the top metallisation to avoid unnecessary optical attenuation due to optical plasmon coupling into metal layers. A first waveguide comprising a layer 1510 of a high refractive index optically transparent material such as tantalum oxide is then evaporated or sputtered on top of the planarising layer 159 (FIG. 15h). The thickness of this layer is selected for the waveguide to support a single transverse mode at the light source wavelength, typically 150 nm in case of tantalum oxide. A decoupling diffraction grating 1511 is then formed on the surface of the first waveguide layer above the photodetector region (FIG. 15i). This grating can be formed for example by a holographic exposure of photoresist followed by dry etching. A coupling layer 1512 of lower refractive index is then deposited on top of the first planar waveguide layer (FIG. 15j). This layer can be made of silicon dioxide and be deposited by evaporation, sputtering or plasma enhanced chemical vapour deposition (PECVD). Alternatively, the coupling layer can be deposited by a spin-coat of a silica solgel material. The advantage of this latter option includes the inherent planarisation of the spin coat step thus preventing the corrugation grating 1512 formed in the first waveguide from being transferred into the second waveguide. Otherwise, this transfer needs to be prevented by a separate planarisation step. The thickness of the coupling layer is selected to be sufficiently small to ensure reasonable coupling over the distance comparable with dimension of the binding site. Conventional beam propagation software can be used to determine the coupling layer thickness. The second waveguide layer 1513 is then deposited similarly to the first waveguide layer (FIG. 15*k*) and an incoupling diffraction grating 1514 is formed in the second waveguide layer similarly to the outcoupling diffraction grating 1511 (FIG. 15*l*). Finally, the grating 1515 is also formed in the second waveguide layer to function as a part of the grating assisted coupler (FIG. 15*m*). To complete the biochip wafer processing a specific binding agent (probe) 1516 is then formed on top of the grating 1515 by one of the available techniques such as robotic spotting, ink jet printing or photolithography. The biochip wafer is then diced into individual chips which are then wirebonded into packages for individual addressing of top and bottom electrodes of the light source/photodetector pairs.

Figure 16:
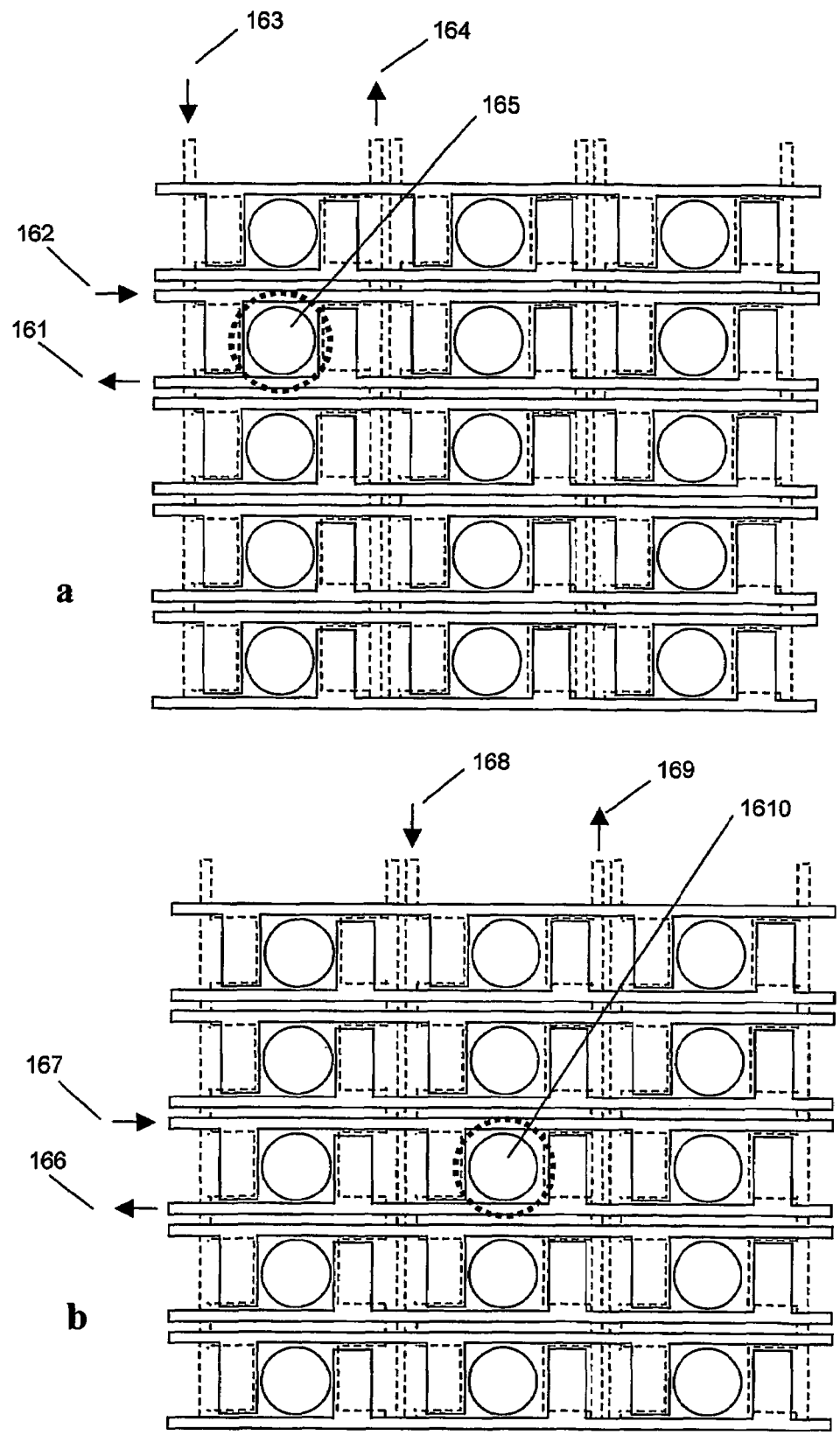
FIG. 16 illustrates a method for testing a biological substance in accordance with the third aspect of the present invention.

FIG. 16 illustrates an embodiment of a third aspect of the present invention comprising a method of testing a biological substance. The biological substance is disposed over a plurality of binding sites whereby each binding site can be interrogated and monitored individually at any point during the hybridisation process independently of the other binding sites. FIG. 16*a* shows monitoring of the site 165 (first in the second raw) by activating the light source through signal applied between electrodes 162 and 163 and receiving signal from the photodetector electrodes 161 and 164 which contains information about the status of hybridisation at site 165. FIG. 16*b* shows monitoring of another site 1610 (second in third raw) by activating light source electrodes 167 and 168 and receiving feedback from photodetector electrodes 166 and 169. In addition to the electrodes shown in FIG. 16 there could be additional electrodes associated with each binding site for controlling hybridisation conditions such as heaters to control hybridisation temperature. The heaters could be made of chromium and located underneath the binding sites, enclosed in a dielectric layer such as silicon dioxide. It is understood that in the layout shown in FIG. 16 a number of alternative means to determine a specific binding event at each binding site could be used as described in this specification earlier.

It will be appreciated by a person skilled in the art that numerous variations and/or modifications may be made to the present invention as shown in the specific embodiments without departing from the spirit or scope of the invention as broadly described. The present embodiments are therefore to be considered in all respects illustrative and not restrictive.

The claims defining the invention (as amended) are as follows:

1. A monolithically integrated biochip for testing biological substances comprising a plurality of binding sites, optical means for determining a specific binding event at each binding site, wherein the plurality of binding sites are monolithically integrated by processing one substrate with the optical means for determining a specific binding event which comprise at least one microcavity light source, at least one photodetector and at least one planar waveguide, an evanescent field of light propagating in the waveguide interacting with the biological substance under test, and wherein the microcavity light source is a photonic band gap microcavity light source.

2. A biochip in accordance with claim 1 wherein either or both the light sources and the photodetectors are implemented in a thin film semiconductor layer.

3. A biochip in accordance with claim 2 wherein the light sources and photodetectors are implemented in the same semiconductor thin film layer.

4. A biochip in accordance with claim 2 wherein the semiconductor thin film material comprises semiconductor polymer.

5. A biochip in accordance with claim 2 wherein the photodetector is a microcavity photodetector.

6. A biochip in accordance with claim 5 wherein the microcavity photodetector is a photonic band gap microcavity photodetector.

7. A biochip in accordance with claim 1 wherein the means for determining a binding event at each site comprise means for determining a refractive index change associated with a binding event.

8. A biochip in accordance with claim 7 wherein the means for determining refractive index change comprise a first planar waveguide on surface of which the binding event occurs, a second planar waveguide located below the first waveguide and separated by coupling layer of lower refractive index than that of the two waveguides.

9. A biochip in accordance with claim 7 wherein the means for determining refractive index change comprise a first planar waveguide on surface of which the binding event occurs, a grating formed in said waveguide, a second planar waveguide located below the first waveguide and separated by coupling layer of lower refractive index than that of the two waveguides.

10. A biochip in accordance with claim 1 wherein the means for determining a binding event further comprise a reference light paths provided at each binding site for error correction.

11. A biochip in accordance with claim 1 wherein the biochip further comprises a plurality of electrodes to control hybridization conditions at each binding site.

12. A biochip in accordance with claim 11 wherein the electrodes comprise resistive heater electrodes formed underneath individual binding sites or groups of biding sites.

* * * * *